United States Patent [19]

Glick

[11] Patent Number: 5,004,615

[45] Date of Patent: * Apr. 2, 1991

[54] METHODS FOR DIAGNOSING, MONITORING AND CONTROLLING THE ONSET AND PROGRESSION OF CERTAIN DEMENTIAS AND IMPEDING MEMORY LOSS OR IMPROVING IMPAIRMENT OF MEMORY

[75] Inventor: J. Leslie Glick, Potomac, Md.

[73] Assignee: Bionix Corporation, Potomac, Md.

[*] Notice: The portion of the term of this patent subsequent to Jan. 15, 2008 has been disclaimed.

[21] Appl. No.: 557,235

[22] Filed: Jul. 25, 1990

Related U.S. Application Data

[60] Continuation of Ser. No. 322,382, Mar. 13, 1989, Pat. No. 4,985,256, which is a division of Ser. No. 203,174, Apr. 27, 1988, Pat. No. 4,837,164.

[51] Int. Cl.$^5$ .................. A61K 33/06; A61K 33/10; C01F 5/02; C01F 5/40

[52] U.S. Cl. .................. 424/692; 424/439; 424/697; 423/635

[58] Field of Search .................. 424/2, 439, 692, 697; 436/79; 423/635

[56] References Cited

U.S. PATENT DOCUMENTS 4,837,164  6/1989  Glick .................. 436/88

Primary Examiner—Thurman Page
Assistant Examiner—C. Azpuru
Attorney, Agent, or Firm—Sughrue, Mion, Zinn Macpeak & Seas

[57] ABSTRACT

Methods for diagnosing, monitoring and controlling the onset and progression of certain dementias, such as AD. The onset and progression of dementia are diagnosed and monitored by following changes in the relative concentrations of two forms of albumin in either serum or CSF. The onset and progression of dementia are controlled and memory loss is impeded or the impairment of memory is improved by dietary supplementation or the administration of Mg.

30 Claims, 3 Drawing Sheets

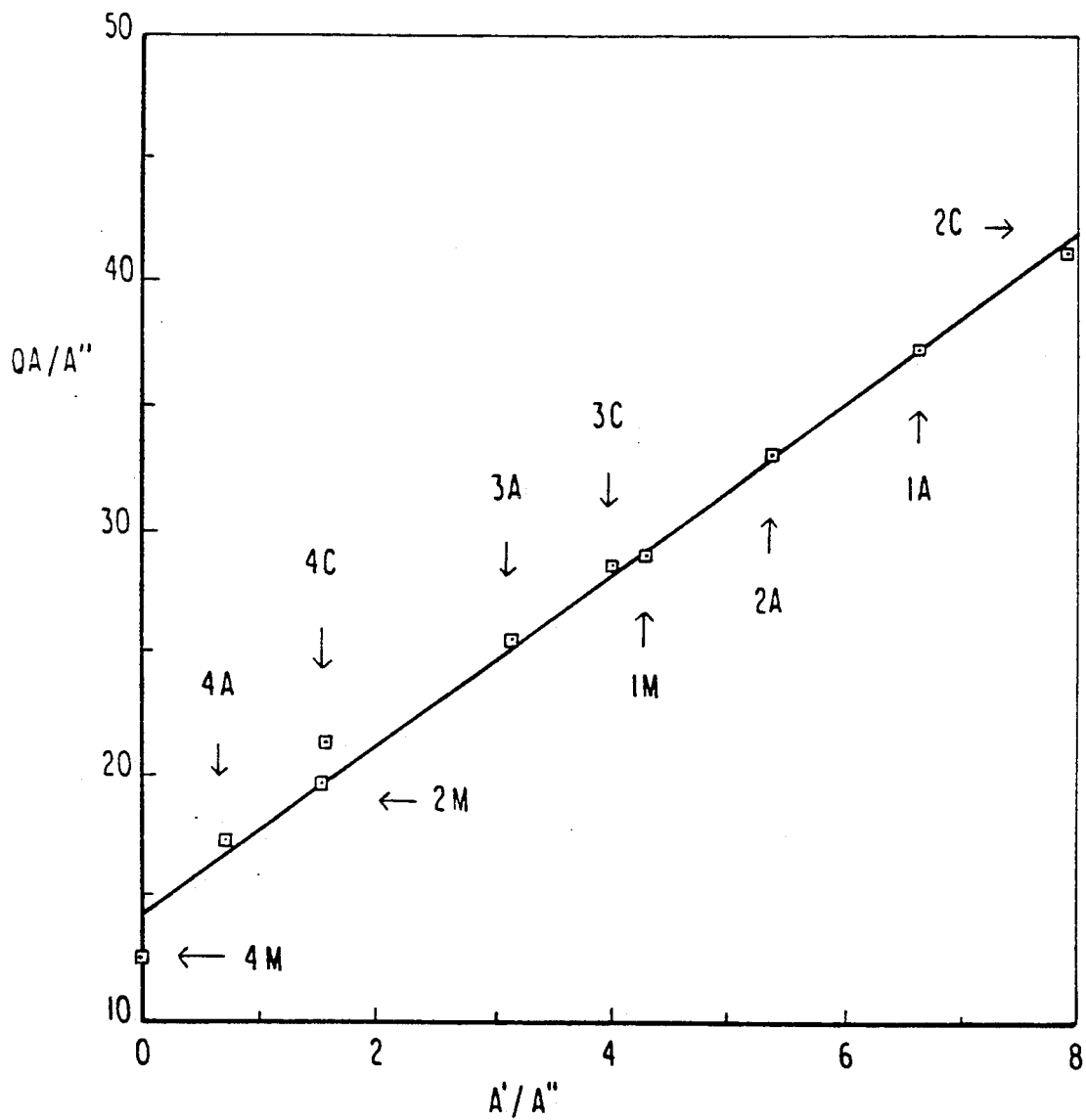

METHODS FOR DIAGNOSING, MONITORING AND CONTROLLING THE ONSET AND PROGRESSION OF CERTAIN DEMENTIAS AND IMPEDING MEMORY LOSS OR IMPROVING IMPAIRMENT OF MEMORY

This is a continuation of application Ser. No. 07/322,382, filed Mar. 13, 1989, which is a Divisional of application Ser. No. 07/203,174, filed Apr. 27, 1988, now U.S. Pat. No. 4,837,164.

FIELD OF THE INVENTION

The present invention relates to methods for diagnosing, monitoring and controlling the onset and progression of certain dementias, such as Alzheimer's disease (AD). The onset and progression of dementia are diagnosed and monitored by following changes in the relative concentrations of two forms of albumin in either serum or cerebrospinal fluid (CSF). The onset and progression of dementia are controlled and memory loss is impeded or the impairment of memory is improved by dietary supplementation or the administration of magnesium (Mg).

BACKGROUND OF THE INVENTION

Dementias affect at least 5-10% of the population over 65 years old, at least 20-30% of the population above the age of 85, and almost half of all patients in U.S. nursing homes (see Folstein, In: *The Principles and Practice of Medicine*, 21st Edition, Harvey, et al, Eds., Appleton-Century-Crofts, pages 379-385 (1984)). AD, which is the most common type of dementia, accounts for half of all diagnosed cases of dementia. The age of onset of AD ranges from 25 to 90 but usually occurs between 70 and 80. The clinical features of AD gradually include amnesia, aphasia, apraxia and agnosia, with death generally occurring 8-10 years after onset of the illness.

AD is generally diagnosed after exclusion of other causes of dementia. Clinical diagnosis of AD is typically only 75-90% correct and is normally verified only upon autopsy (see Davies, *Neurobiol. Aging*, 7:459-466 (1986)). In particular, in the early stages of the disorder, the diagnosis of AD and other dementias, such as multi-infarct dementia (MID) and Creutzfeldt-Jakob disease (CJD), is problematic. Not only is it difficult to distinguish these irreversible dementias from each other, but also, it is difficult to distinguish them from reversible dementia disorders, such as hypothyroidism, depression, hydrocephalus, brain tumors and thiamine deficiency. While physiologic testing, electroencephalography and computerized tomography are useful, they are non-specific diagnostic tools.

Although some types of dementia, e.g., those resulting from depression, nutritional disorders, and endocrine disorders, are curable, for most cases, including AD, MID, CJD and Huntington's disease (HD), there is at present no cure.

Brain levels of Mg are reduced in alcoholics, in comparison to non-alcoholics (see Zumkley, et al, *Magnesium-Bull.*, 8:284-287 (1986)) and evidence indicates that alcohol-induced, long term Mg depletion is probably a prerequisite factor in human fatalities associated with cobalt toxicity resulting from cobalt-supplemented beer (see Marier, *Magnesium-Bull.*, 8:293-296 (1986)). However, these observations have not previously been related to the pathogenesis of dementias.

It has been pointed out that brain ischemia or stroke-like events result in rapid neuronal losses of Mg and potassium (K), followed by uptake of sodium (Na) and calcium (Ca). Stroke patients are deficient in serum and CSF Mg levels. In experimental animals, acute Mg deficiency results in excess Ca uptake into the brain and in the occurrence of cerebrovasospasms. In clinical studies, infusion of Mg appears to alleviate cerebrovasospasms. Further, consumption of foods relatively high in Mg and K and low in Na appear to be associated with a lower than normal incidence of strokes (see Altura, et al, *Magnesium*, 3:195-211 (1984)). However, again, these observations have not previously been related to the pathogenesis of dementias.

Hypomagnesemic encephalopathy, which involves dementia, is correlated with low plasma Mg levels. This disorder is treatable with intramuscular administration of Mg, regardless of what led to the underlying Mg depletion (see Cohen, *Magnesium*, 4:203 (1985)). Heretofore, this type of disorder has not been suggested as one having an etiology, pathogenesis or response to treatment in common with most other dementias, including AD, MID, CJD and HD. These dementias are not characterized by low levels of Mg in plasma or CSF.

The increased incidence in the elderly of various chronic diseases associated with Mg depletion has been linked to insufficient daily intake of Mg, decreased intestinal absorption of Mg, and increased usage of pharmacologic agents which, as a side effect, enhance Mg excretion from the body (see Mountokalakis, *Magnesium*, 6:5-11 (1987)). However, these observations have not previously been related to the pathogenesis and possible treatment of dementias, as dementias generally have not been considered as diseases marked by an insufficiency of Mg.

On the other hand, Mg insufficiency may contribute to the progression of dementias, AD and HD are associated with an abnormally low level of Mg in brain neurons (see Korf, et al, *Prog. Brain Res.*, 70:213-226 (1986)). However, Korf, et al, supra, did not view insufficiency of Mg as a key pathological event but, rather, as part of a pattern of cation changes in certain areas of the brain, including increases in intracellular Na and decreases in intracellular K. These cation changes were viewed as secondary to changes in neurotoxic and excitatory amino acids in brain cells of AD and HD patients.

AD and the amyotrophic lateral sclerosis and Parkinsonism-dementia complex of Guam (ALS-PD) are associated with an abnormally high level of aluminum (Al) in brain neurons (see Perl, et al, *Science*, 208:297-299 (1980); Perl, et al. *Science*, 217:1053-1055 (1982)). It has been suggested by the present inventor that the increased level of Al in the brain, which is associated with these dementias, causes or contributes to an insufficiency of Mg since Al inhibits Mg-requiring enzymes.

In this connection, it has been hypothesized that increased levels of Ca in brain cells of aging rats are responsible for impairing learning (see Landfield, In: *Treatment Development Strategies for Alzheimer's Disease*, Crook, et al, Eds., Mark Powley Associates, pages 221-243, Madison, Conn. (1986)). Mg was administered as a Ca-blocking agent to aged rats, since Mg is a competitive inhibitor of the synaptic actions of Ca. However, these studies with aged rats have suggested to the present inventor a causal relationship involving an apparent deficiency of Mg in brain neurons and impaired maze reversal learning, i.e., treatment of the rats with Mg improves maze reversal learning. While it has been suggested that the level of Ca may be elevated in brain cells of AD patients, Korf, et al, supra, observed no changes in the level of brain levels of Ca, although decreases were seen in the brain levels of Mg, in AD and HD patients.

SUMMARY OF THE INVENTION

Accordingly, an object of the present invention is to provide a method for diagnosing the onset of dementias, such as AD, prior to the appearance of clinical symptoms.

Another object of the present invention is to provide a method for monitoring the progression of dementias, such as AD, and a method for monitoring the efficacy of a palliative approach towards clinical management of the disease so to optimize such.

Still another object of the present invention is to provide a palliative method for treatment of dementias, such as AD.

A further object of the present invention is to provide a prophylactic method for delaying the onset and mitigating the development of clinical symptoms of dementias, such as AD.

A still further object of the present invention is to provide a method for impeding memory loss or improving impairment of memory.

These and other objects of the present invention will be apparent from the detailed description of the invention provided herewith.

In one embodiment, the above-described objects of the present invention have been met by a method for diagnosing the onset of certain dementias, such as AD, MID, HD and ALS-PD, preferably AD and MID, prior to the appearance of clinical symptoms of disease by following changes in the relative concentrations of two forms of albumin in either serum or CSF. The method also permits periodic monitoring of the progression of these dementias, either untreated or in response to the administration of dietary supplements and/or orally, parenterally or similarly administered anti-dementia agents.

In other embodiments, the above-described objects of the present invention have been met by a prophylactic method for preventing or delaying the onset of such dementias, a palliative method for the treatment of dementias, and a method for impeding the loss of memory or improving impairment of memory, which comprise dietary supplementation or the administration of Mg alone or in combination with another anti-dementia or anti-memory loss agent.

BRIEF DESCRIPTION OF THE DRAWING FIGURES

FIG. 1 illustrates the relationships between albumin and immunoglobulin G (IgG) concentrations in CSF, and albumin and IgG quotients. In FIG. 1, open and solid symbols represent mean albumin and IgG values, respectively, which were reported by four different laboratories for control, AD, and MID groups. The albumin data are labeled C, A, M for control, AD, and MID groups, respectively, and 1, 2, 3, 4 for the laboratories reporting the data. The laboratories are as follows: laboratory 1 (see Elovaara, et al, *J. Neurol Sci.*, 70:73–80 (1985); and Elovaara, et al, *Eur. Neurol.*, 26:229–234 (1987)); laboratory 2 (see Leonardi, et al, *J. Neurol. Sci.*, 67:253–261 (1985)); laboratory 3 (see Kay, et al, *Neurobiol. Aging*, 8:21–25 (1987)); and laboratory 4 (see Alafuzoff, et al, *J. Neurol. Sci.*, 60:465–472 (1983)). All laboratories reported data for control and AD groups, and all but one (laboratory 3) reported data for MID groups. R is the correlation coefficient, and P is the probability that the variables are independent of each other.

FIG. 2 illustrates the relationships between albumin and IgG concentrations in CSF, and albumin and IgG concentrations in serum. The symbols and laboratories in FIG. 2 are as identified in FIG. 1.

FIG. 3 is a graphical illustration of the correspondence fit of the albumin data of FIGS. 1 and 2 to a simple regression curve. The symbols and laboratories in FIG. 3 are as identified in FIG. 1. The control group, 1C, is not represented in FIG. 3 because its value for A" equals zero, and therefore both QA/A" and A'/A" are infinite.

DETAILED DESCRIPTION OF THE PREFERRED EMBODIMENTS

Figure 1:
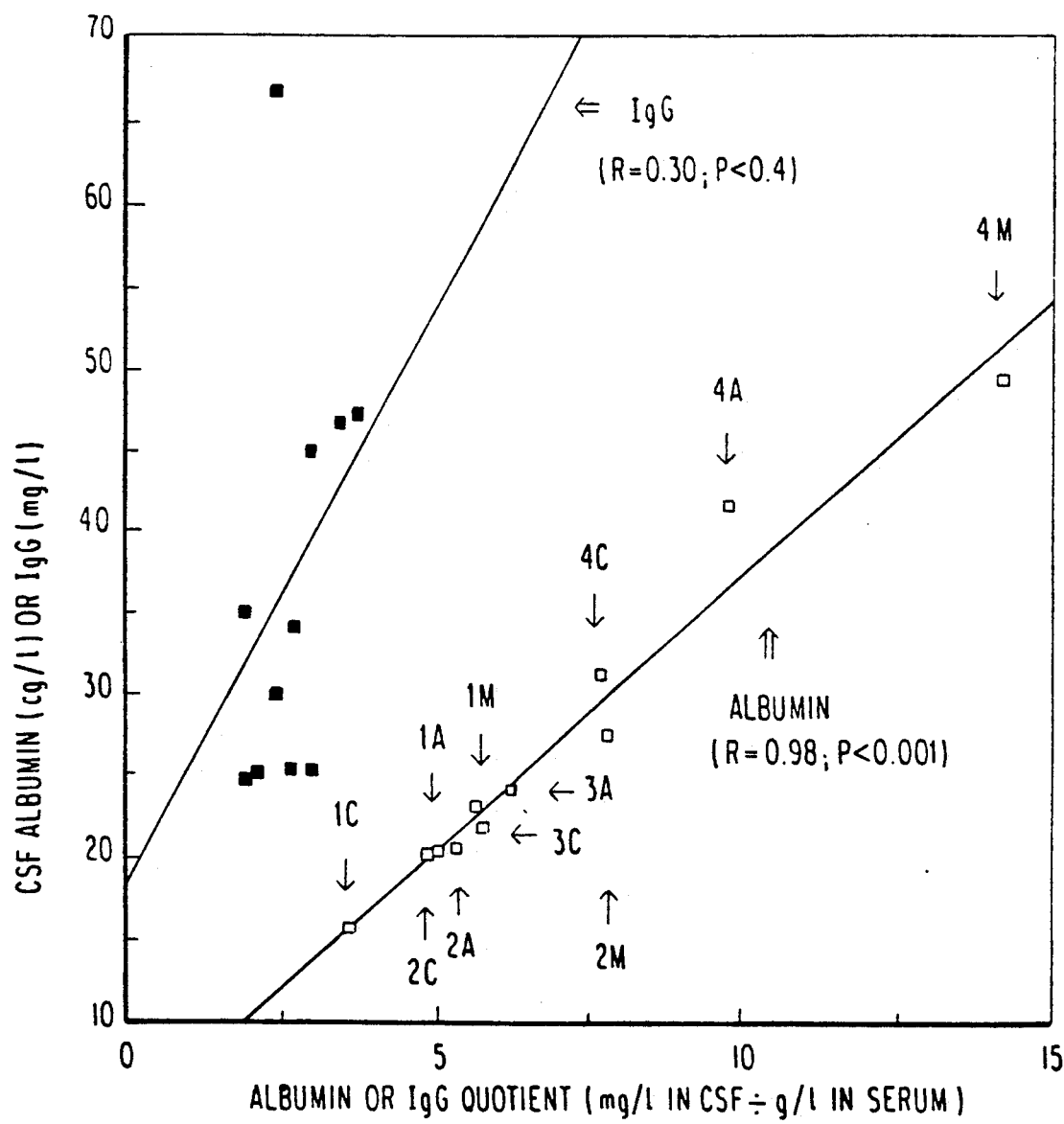

As discussed above, in one embodiment, the above-described objects of the present invention have been met by a method for diagnosing the onset of certain dementias, such as AD, MID, HD and ALS-PD, preferably AD and MID, prior to the appearance of clinical symptoms of disease. The method also permits periodic monitoring of the progression of these dementias, either untreated or in response to the administration of dietary supplements and/or orally, parenterally or similarly administered anti-dementia agents.

The onset and progression of the dementia are monitored by following changes in the relative concentrations of two forms of albumin in either serum or CSF. The technique disclosed herein enables the concentrations of the two forms of serum albumin to be estimated either from the total serum and CSF albumin concentrations, or by a procedure which measures the affinities of Mg and Al to serum albumin. The procedure also permits the total CSF concentration of albumin to be estimated from the concentrations of the two forms of serum albumin, thus eliminating the need for CSF-invasive procedures.

In other embodiments, the above-described objects of the present invention have been met by a prophylactic method for preventing or delaying the onset of such dementias, a palliative method for the treatment of dementias, and a method for impeding the loss of memory or improving impairment of memory, which comprise dietary supplementation or the administration of Mg alone or in combination with another anti-dementia or anti-memory loss agent.

The present invention results from the discovery that increases in the total concentration of CSF albumin in subjects afflicted with dementias, such as AD and MID, may be due to the increased presence of an altered form of albumin relative to the normal form of albumin generally present. While not desiring to be bound, it is believed that the altered albumin form physically differs from the normal albumin molecule in some manner which enhances the ability of the former molecule to cross the blood-brain barrier into CSF. CSF albumin originates from the serum, although present in the former in much lower concentration. As altered albumin is considered to have the ability to cross the blood-brain barrier more readily than the normal albumin molecule, the concentration of the normal form of CSF albumin, as a percentage of the total CSF albumin, would be expected to decrease in AD and MID patients.

Again, while not desiring to be bound, it is also believed that the altered form of albumin competes with the normal form in binding to brain neurons, and binds Al with a greater affinity than Mg, in contrast to the normal albumin form, which binds Mg with greater affinity than Al. The binding of the altered albumin form facilitates Al uptake by the neurons and at the same time impedes Mg uptake, accounting for the observed increased presence of Al in the neurons of brain tissue obtained from AD subjects, and the depletion of Mg in the neurons of such subjects, relative to control patients of similar ages.

It has been found in the present invention that upon applying statistical analysis to the data of Perl, et al, *Science*, 208:297-299 (1980), there is a statistically significant decrease in the levels of Mg in brain neurons in AD patients, compared to that in control patients. This analysis and the resulting conclusion were not reported by Perl, et al, supra.

The Diagnostic and Monitoring Methods

In the present invention, a method has been developed whereby the relative levels of normal albumin and altered albumin in the serum are estimated and are tracked over time as an indicator of the onset and progression of certain dementias. At present, normal albumin and the postulated altered albumin form have not been differentiated, and accordingly the procedural technique developed herein is largely analytical in nature.

By way of background, FIG. 1 illustrates the relationship between the albumin and IgG concentrations in CSF and the albumin and IgG quotients (each quotient is the ratio of mg/l albumin or IgG in CSF to g/l of the same in serum). Open symbols represent mean albumin values reported by four different laboratories for control, AD, and MID groups. Solid symbols represent similar means for IgG values. Albumin data are labeled C for control, A for AD, and M for MID groups, respectively. Numerals 1-4 are indicative of the laboratory reporting the data (no MID data was reported for laboratory 3). Also in the figure, R indicates the correlation coefficient, higher values representing higher correlation, and P is the probability that the variables are independent of each other.

FIG. 1 demonstrates a very good fit between the albumin quotient and the CSF concentration of albumin over a substantially wide range of quotient values, in spite of the fact that the data used in FIG. 1 represent mean values obtained by four different laboratories. On the other hand, the IgG quotient is relatively constant regardless of the amount of IgG in CSF. FIG. 1 indicates the presence of at least two forms of albumin. If the ability of albumin to penetrate the blood-brain barrier were to be affected by a change in the blood-brain barrier permeability to serum proteins, rather than by a specific change in the molecular structure of albumin, one would not expect to see a correlation between the albumin quotient and the concentration of CSF albumin in the absence of a similar correlation between the IgG quotient and the concentration of CSF IgG. One possible change in the molecular structure of albumin which would explain the observed data would be a decrease in the hydrodynamic radius of the albumin molecule. An inverse correlation has previously been seen between the hydrodynamic radius and the ratio of CSF/serum concentrations for a number of serum proteins.

Figure 2:
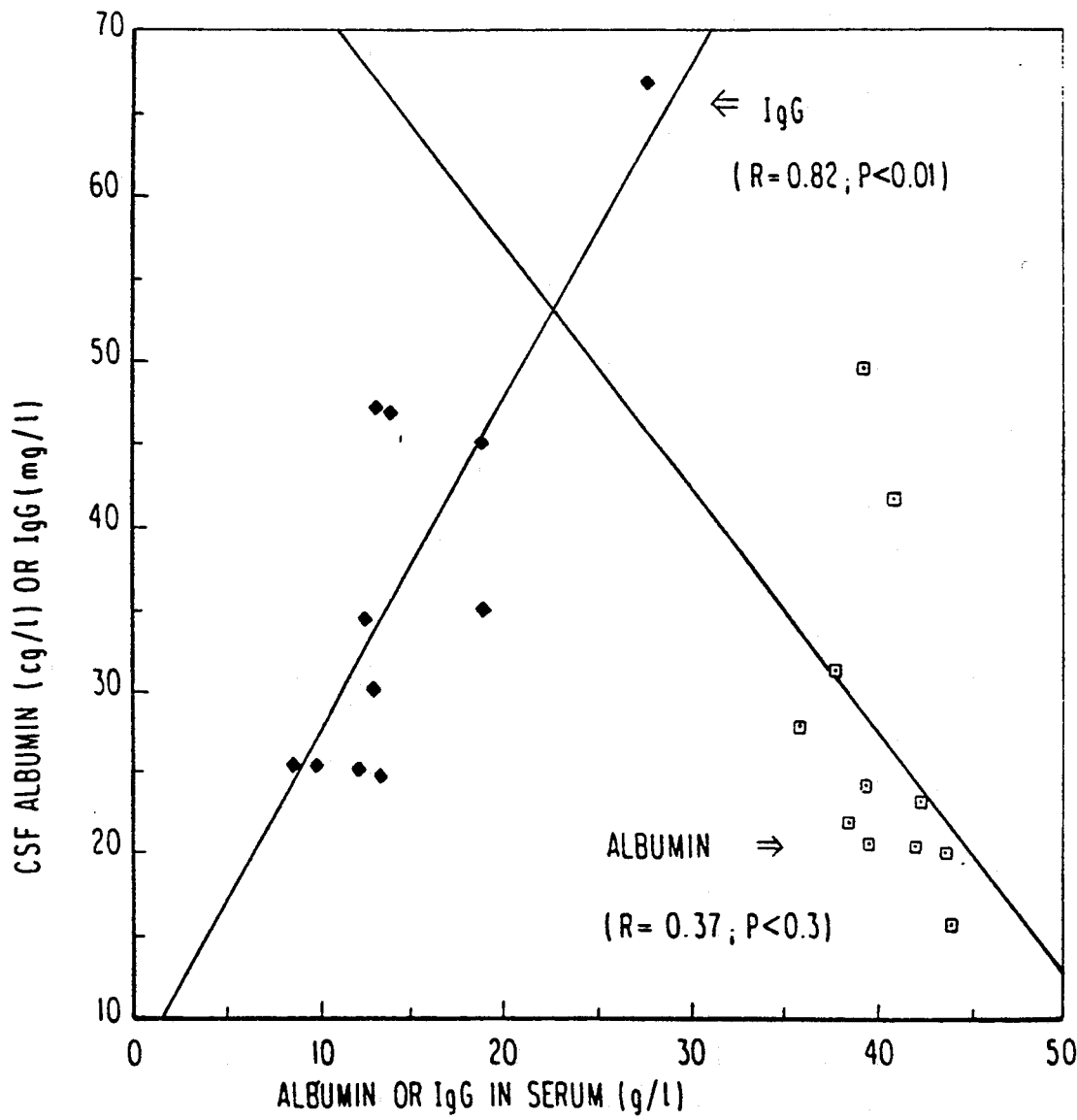

FIG. 2 illustrates that, in contrast to the relationship between the concentration of IgG in CSF and that in serum, there is poor correlation between the concentration of albumin in CSF and that in serum. The relationship between the CSF concentration of albumin and the albumin quotient is thus independent of the serum concentration of albumin. The correlation between the CSF concentration of albumin and the albumin quotient is therefore considered to be dependent upon the percentage of altered albumin molecules in the total serum albumin population. As noted above, the data of FIG. 1 indicates that the relationship between CSF concentration of albumin and the albumin quotient is not a function of the state of the blood-brain barrier, the other candidate for explaining the CSF albumin concentration-albumin quotient correlation. That is, the results of FIGS. 1 and 2 taken together indicate that the degree to which albumin penetrates the blood-brain barrier is more dependent upon a specific change in the molecular structure of albumin than on a change in the blood-brain barrier permeability to serum proteins.

A process for estimating the amounts of normal albumin and altered albumin will now be described, with reference to the data contained in FIGS. 1 and 2. If both forms of albumin exist in serum and in CSF, equations (1) and (2) apply.

$$A = A' + A''  \quad (1)$$

$$QA = Q'A' + Q''A'' \quad (2)$$

In the above equations, A represents the total serum concentration of albumin, and $A''$ and $A''$ respectively represent the serum concentrations of normal albumin and altered albumin. Values $QA$, $Q'A'$, and $Q''A''$ represent, respectively, the total CSF concentration of albumin, the CSF concentration of normal albumin, and the CSF concentration of altered albumin. $Q$, $Q'$ and $Q''$ represent albumin quotients, specifically, the total albumin quotient, the normal albumin quotient and the altered albumin quotient, respectively. Each quotient represents the ratio of the concentration of the relevant albumin in CSF to that in the serum. Values of A and QA are directly measurable using known techniques as disclosed, for example, in Elovaara, et al, *J. Neurol Sci.*, 70:73-80 (1985). Values of Q are readily determinable by calculating the ratio QA/A.

Given that altered albumin crosses the blood-brain barrier more effectively than normal albumin, $Q''$ is greater than $Q'$. Default values of these two quantities can be determined empirically from FIG. 1. Specifically, when $A''$ equals 0, which perhaps occurs in some healthy individuals, $A = A'$ and $Q = Q'$. On the other hand, when $A' = 0$, which perhaps occurs in some AD and MID individuals, $A = A''$ and $Q = Q''$. Thus, $Q'$ represents the lowest possible value for Q, while $Q''$ represents the highest possible value for Q. Referring to FIG. 1, the lowest and highest mean values for Q were 3.6 mg/g, representing a control group, and 14.2 mg/g, representing an MID group. It is assumed that the mean values shown in FIG. 1 cannot represent absolute lowest and highest values for Q, since these values are, after all, means. Therefore, $Q'$ is actually somewhat less than 3.6 mg/g, while $Q''$ is greater than 14.2 mg/g. To simplify, however, $Q'$ and $Q''$ will be set equal to 3.6 mg/g and 14.2 mg/g respectively for the following calculations. A manner of refining the default values is described below in connection with equation (5). Simultaneous solution of equations (1) and (2) using the default values for $Q'$ and $Q''$ results in the following:

$$A' = A(Q - Q')/(Q'' - Q'); \quad (3)$$

$$A'' = A(Q - 3.6)/10.6 \quad (4)$$

Using the foregoing equations, a plurality of values can now be computed, including $A'$, $A''$, $A'/A''$, $A''/A$, $Q'A'$, $Q''A''$, $Q'A'/Q''A''$, and $Q''A''/QA$.

The Table below tabulates estimated serum and CSF concentrations for both normal and altered forms of albumin which would be associated with the control, AD, and MID groups whose total albumin concentrations and quotients are given in FIGS. 1 and 2. The mean values of $A'$ and $A''$ are obtained for each of the three groups by calculating $A''$ and $A'$ from equations (4) and (1), respectively, for each pair of A and Q values reported for that group by an individual laboratory, and then averaging for each group the calculated $A'$ and $A''$ values. Similar computations are employed and the default values for $Q'$ and $Q''$ are used to obtain the values of $Q'A'$ and $A''A''$.

TABLE

| Group | Normal albumin concentration | | Altered albumin concentration | | Altered albumin fraction[a] | |
|---|---|---|---|---|---|---|
| | Mean (units/l)[b] | % control | Mean (units/l) | % control | Mean (%) | % control |
| Serum | | | | | | |
| Control | 34.1 | 100 | 6.8 | 100 | 17.5 | 100 |
| AD | 29.1 | 85 | 11.3 | 166 | 27.9 | 159 |
| MID | 18.6 | 55 | 20.4 | 300 | 52.8 | 302 |
| CSF | | | | | | |
| Control | 123 | 100 | 96.3 | 100 | 38.5 | 100 |
| AD | 105 | 85 | 160 | 166 | 55.1 | 143 |
| MID | 67.0 | 54 | 290 | 301 | 73.3 | 190 |

[a] Altered albumin concentration divided by the sum of the normal and altered albumin concentrations
[b] Units represent g and mg for albumin concentrations in serum and CSF, respectively As expected, the Table above indicates that, compared to the control group, both the AD and MID groups exhibit lower concentrations of normal albumin and higher concentrations of altered albumin in both serum and CSF.

Equation (2) may be transformed to obtain a simple regression curve as follows:

$$QA/A'' = Q'(A'/A'') + Q'' \quad (5)$$

Assuming the above values for $Q'$ and $Q''$, $QA/A''$ and $A'/A''$ may be computed from the data presented in FIGS. 1 and 2. FIG. 3 illustrates the linear relationship between $QA/A''$ and $A'/A''$. For a given laboratory, $QA/A''$ and $A'/A''$ were highest for the control group, as would be expected. The values were lower for the AD group and lowest for the MID group. The curve (shown in FIG. 3) which best fits the data has a slope of 3.5 and a y intercept of 14.4. As is apparent from the form of equation (5), ($y = mx + b$), the y intercept is $Q''$ and the slope is $Q'$. The values of $Q' = 3.5$ and $Q'' = 14.4$ are close to the previously assumed values of $Q' = 3.6$ and $Q'' = 14.2$. Revised values of $Q'$ and $Q''$ can be obtained in this manner for those patient populations for which individual $A'/A''$ and $QA/A''$ ratios are given or can be measured.

It is next desired to formulate the relationships among the total serum albumin-Al binding constant (a) (micrograms ($\mu$g) of Al/g of albumin), the normal ($a'$) and altered ($a''$) albumin-Al binding constants, similar values m, $m'$ and $m''$ for Mg (milligrams (mg) of Mg/g of albumin), and the values A, $A'$ and $A''$ for serum albumin concentrations. To estimate $a'$, $a''$, $m'$ and $m''$, equations (6) and (7) are applicable, and equations (8) and (9) are readily derived.

$$aA = a'A' + a''A'' \quad (6)$$
$$mA = m'A' + m''A'' \quad (7)$$
$$aA/A'' = a'(A'/A'') + a'' \quad (8)$$
$$mA/A'' = m'(A'/A'') + m'' \quad (9)$$

Values of a and m for various individuals are obtained using previously established techniques (see Prasad, et al. *J. Lab. Clin. Med.*, 54:357-364 (1959); Kroll, et al, *Clin. Chem.*, 31:244-246 (1985); King, et al, *Res. Comm. Chem. Path. Pharmacol.*, 26:161-169 (1979); and Trapp, *Life Sciences*, 33:311-316 (1983)). At the same time, values of the total CSF albumin-Al binding constant (a) ($\mu$g of Al/g of albumin) and the total CSF albumin-Mg binding constant (m) (mg of Mg/g of albumin) can be obtained using similar techniques. Values for A and QA are measured, as described above, so that ratios $A/A''$ and $A'/A''$ for these individuals can be computed using equations (1), and (3) or (4). Equation (4) is substituted for equation (3) if the first-mentioned default values for $Q'$ and $Q''$ are used. In accordance with equation (8), values of $aA/A''$ versus $A'/A''$ are plotted to allow determination of $a'$ from the slope and $a''$ from the y intercept. Similarly, in accordance with equation (9), $mA/A''$ is plotted versus $A'/A''$ to determine m from the slope and $m''$ from the y intercept. Default values for $a'$, $a''$, $m'$ and $m''$ are thus obtained.

Upon dividing equation (6) by equation (7), equation 10 may be obtained, and equation 11 readily follows.

$$a/m = (a'A' + a''A'')/(m'A' + m''A'') \quad (10)$$

$$A'/A'' = (ma'' - am'')/(am' - ma') \quad (11)$$

It will be appreciated that equation (11) yields the ratio of normal serum albumin concentration to altered serum albumin concentration in terms of easily measured serum albumin-Al and -Mg binding constants a, m and the four default values for $a'$, $a''$, $m'$ and $m''$. Using this equation, the ratio of $A'/A''$ can subsequently be determined for other individuals (e.g., individual patients) without the requirement of measuring QA, i.e., without the necessity of drawing CSF fluid from the patient. The quantity A is next measured for such other individuals. Since equation (1) may be transformed to equation (12), and equation (13) readily follows, $A'$ and $A''$ can be computed by means of equations (1) and (13).

$$A = A''(A'/A'') + A'' \quad (12)$$

$$A'' = A/(A''/A\Delta + 1) \quad (13)$$

The CSF ratio of normal albumin concentration to that of altered albumin ($Q'A'/Q''A''$) can also be obtained by applying the default values for $Q'$ and $Q''$, and multiplying $A'/A''$ by $Q'/Q''$. QA can then be computed in accordance with equation (2). Alternatively, the percentage of total albumin existing in the altered form in either serum or CSF could be computed. Since ratios $A'/A''$, $Q'A'/Q''A''$, $A''/A$ and $Q''A''/QA$ will vary in accordance with the relative concentration of altered albumin, they are useful as indicators of the onset of dementia such as AD or MID. Particularly, once a healthy baseline value of, for example, $A'/A''$ is established for a healthy individual, a decreasing ratio of this value over time could signal the onset of dementia prior to the appearance of clinical symptoms. An increasing ratio of $A''/A$ or $Q''A''/QA$ or a decreasing ratio of $Q'A'/Q''A''$ could act as an equivalent indicator.

The accuracy of the calculated ratios $A'/A''$, $A''/A$, etc. are substantially dependent upon the original determination of suitable default values for $Q'$ and $Q''$, as is evident from equation (3) in particular. One manner of determining appropriate $Q'$, $Q''$ values was explained above in connection with equation (5). When future assay methods are developed to directly measure the serum concentrations of normal and altered albumin, the ratio $A'/A''$ could be directly determined and $QA/A''$ could be measured for a number of individuals. The resulting data, when plotted in the form shown in FIG. 3, would yield very accurate values of $Q'$ and $Q''$ from the slope and y intercept. Since $Q'$ and $Q''$ are constants, one could then use their values to compute either QA, or $A'$ and $A''$ in subsequent tests upon individuals in which direct measurements are not made of either QA, or $A'$ and $A''$. The ability to calculate CSF values such as QA without direct measurement is advantageous, since direct measurement of this parameter requires the withdrawal of CSF fluid.

Revised values of $Q'$ and $Q''$ can also be obtained through the calculation of certain ratios of the albumin-Al and -Mg binding constants. Equations (14) and (15) indicate the relationships among the binding constants and the values of QA, $Q'A'$ and $Q''A''$:

$$aQA = a'Q'A' + a''Q''A'' \tag{14}$$

$$mQA = m'Q'A' + m''Q''A'' \tag{15}$$

where a designates the total CSF albumin-Al binding constant and m indicates the corresponding constant for Mg, as mentioned above. The ratio of m/a can be obtained by dividing equation (15) by equation (14):

$$m/s = (m'Q'A' + m''Q''A'')/(a'Q'A' + a''Q''A'') \tag{16}$$

The ratio of a/m was given by equation (10). The binding constant ratio R results from the multiplication of equations (10) and (16):

$$R = am/ma \tag{17}$$

$$R = \frac{(a'A' + a''A'')(m'Q'A' + m''Q''A'')}{(m'A' + m''A'')(a'Q'A' + a''Q''A'')} \tag{18}$$

The ratio R can be calculated for any given individual; of greatest interest will be the values of R which approach 1. The reason for this is that $R=1$ when either $A=A''$ or $A=A'$, as can be verified from equation (18). A value of $R=1$ therefore indicates that either $A'=0$ or $A''=0$, with reference to equation (1). As indicated previously, and from equation (2), this implies that either $Q=Q''$ or $Q=Q'$.

The value of R is computed using the measured values which appear in equation (17). When a sample is obtained having an R value equal to 1, the value of Q for this sample then becomes the default value for either $Q'$ or $Q''$. Which of the default values should be reset will be self-evident from the value of Q. If Q is at the low end of the range of Q values, the default value for $Q'$ will be set to Q, and if Q is at the high end of the range of Q values, the default value for $Q''$ will be set to Q. With a significantly large sample population, it is expected that values of both $Q'$ and $Q''$ can be accurately determined in this manner.

Prophylactic and Palliative Methods

As discussed above, in other embodiments, the present invention relates to prophylactic and palliative methods for controlling the onset and progression of dementias, which may be used in conjunction with the diagnostic and monitoring methods. The monitoring method serves as a prognostic indicator of the efficacy of the palliative method. The present invention also relates to a method for impeding loss of memory or improving the impairment of loss of memory. These methods involve administering, to a healthy subject or to a dementia or memory loss subject. Mg alone or in combination with another anti-dementia or anti-memory loss agent.

The normal dietary intake of Mg in a healthy adult subject is about 200 to 450 mg/day, more generally about 300 to 350 mg/day, whereas in a subject afflicted with dementia such as AD, MID, HD or ALS-PD, or in a subject afflicted with memory loss, the dietary intake of Mg may be reduced to below normal levels. Alternatively, such a subject may suffer from impaired intestinal absorption or increased excretion of Mg. Still alternatively, such a subject may require a higher than normal intake of Mg to offset the deleterious affects resulting from the accumulation of neurotoxic substances, such as Al, or to compensate for impaired transport of Mg in brain tissue.

Thus, as to a subject with dementia or memory loss whose dietary intake of Mg is below normal, the above-described methods of the present invention comprise oral administration of Mg, such that the supplementary daily intake of Mg is about 200 to 1,620 mg/day, preferably about 300 to 1,260 mg/day.

Furthermore, as to a subject with dementia or memory loss whose dietary intake of Mg is normal, the above-described methods of the present invention comprise oral administration of Mg, such that the supplemental daily intake of Mg in the subject is about 12 to 18 mg/kg of body weight, or about 540 to 1,620 mg/day, preferably about 840 to 1,260 mg/day.

Mg can be administered orally to the subject in the form of a food containing high concentrations of Mg, such as regular or skim milk; cereals such as cream of wheat, oatmeal, bran flakes, puffed wheat and shredded wheat; whole wheat bread; juices such as grape juice, grapefruit juice, orange juice, pineapple juice, prune juice and tomato juice; vegetables such as asparagus, broccoli, peas, beets, carrots, corn, tomatoes and potatoes; fruits such as bananas, cherries, oranges and pineapples; shrimp; and mixtures thereof.

The amount of food containing high concentrations of Mg which must be consumed per day by the subject will vary depending on the concentration of Mg in the particular food type. For example, when the subject consumes a meal consisting of a medium size banana, a half a cup of bran flakes, a cup of regular milk, and a slice of whole wheat bread, which meal contains about 110 to 125 mg of Mg, this amount of Mg represents about 7 to 60% of the supplementary daily intake which should be consumed by the subject to reach the above-discussed levels of orally administered Mg.

In addition, Mg can be orally administered using a pharmaceutically acceptable Mg compound which allows Mg to be freely available in the subject. Examples of such pharmaceutically acceptable Mg compounds include Mg sulfate, Mg lactate, Mg oxide, Mg chloride, Mg citrate, Mg hydroxide, and mixtures thereof.

Alternatively, in advanced states of dementia, the Mg can be administered parenterally, such as intravenously or intramuscularly, to the subject in the form of the above-described pharmaceutically acceptable Mg compounds, preferably Mg sulfate, but at lower dosages than the oral dosages, generally about 70 to 540 mg/day, preferably about 100 to 500 mg/day.

Examples of the another anti-dementia or anti-memory loss agent which can be administered with the Mg (whether in the form of a food containing high concentrations of Mg or whether in the form of a pharmaceutically acceptable Mg compound) include: an agent which removes Al from the body, such as sodium fluoride (NaF) or desferrioxamine (DFO); an anti-acetylcholine esterase agent, such as tetrahydroaminoacridine (THA) or physostigmine; an agent which provides a source of choline for acetylcholine synthesis, such as lecithin or choline chloride; and mixtures thereof.

NaF removes Al from the body by lowering Al levels in serum (see Liss, et al, *Neurobiol. Aging*, 7:552-554 (1986)). DFO, as a trivalent metal chelating agent, also lowers Al levels in serum (see Crapper McLachlan, et al, *Amer. J. Kidney Diseases*, 6:322-329 (1985)). The importance of the reduction of Al levels in serum is discussed in detail below.

Brain levels of Al are increased above normal in a subject afflicted with dementia such as AD or ALS-PD. Al inhibits Mg-activated enzymes, including those involved in the production of acetylcholine (see Siegel, *Amer. J. Kidney Diseases*, 6:353-357 (1985); and Trapp *Kidney International*, 29:s12-16 (1986)). Thus, in one embodiment of the method of the present invention, an agent which removes Al from the body is also administered to a subject with dementia or memory loss such that the level of Al in the brain of the subject is either lowered or inhibited from accumulating further. As discussed above, along with supplementation of Mg as described above, the amount of Al in a subject can be lowered or inhibited from accumulating further using NaF or DFO.

Generally, the amount of NaF to be administered orally in order to lower the level of Al in the serum is about 0.5 to 1.0 mg/kg of body weight/day, preferably about 40 to 60 mg/day.

Generally, the amount of DFO to be administered intramuscularly in order to lower the level of Al in the serum is about 5 to 20 mg/kg of body weight every 2 days, preferably 5 to 10 mg/kg of body weight every 2 days.

In other embodiments of the method of the present invention, an agent which inhibits acetylcholine esterase activity and therefore breakdown of acetylcholine, and an agent which provides a source of choline for acetylcholine synthesis are administered to a subject afflicted with dementia, such as AD or ALS-PD, along with supplementation of Mg as described above. A subject afflicted with AD suffers from depletion of acetylcholine in the brain (see Perry, *Brit. Med. Bull.*, 42:63-69 (1986). An anti-acetylcholine esterase such as THA or physostigmine and a source of choline such as lecithin or choline chloride can cause improved performance in memory testing as well as other symptomatic improvements in a subject afflicted with AD (see Summers, et al. *New England J. Med.*, 315:1241-1245 (1986)).

Generally, the amount of THA required for oral administration is about 25 to 200 mg/day, preferably about 150 to 200 mg/day over sustained periods.

THA may also be administered intravenously in an amount of about 0.25 mg/kg of body weight to 1.5 mg/kg of body weight, preferably about 1.0 to 1.5 mg/kg of body weight, not more than once a day.

Generally, the amount of physostigmine required for oral administration is about 2 to 16 mg/day, preferably about 4 to 16 mg/day, divided in 6 to 8 doses per day.

Physostigmine may also be administered intravenously in an amount of about 0.2 to 1.0 mg/day, preferably about 0.3 to 0.8 mg/day.

Generally, the amount of lecithin or choline chloride orally administered is about 1200 to 14,400 mg/day, preferably about 9,600 to 12,000 mg/day.

When side effects occur with the above therapies, such as nausea and emesis, a peripheral anticholinergic agent, such as glycopyrrolate or methscopolamine bromide, can be administered to eliminate the side effects. Glycopyrrolate can be administered orally while methscopolamine can be administered subcutaneously or intramuscularly.

While the invention has been described in detail and with reference to specific embodiments thereof, it will be apparent to one skilled in the art that various changes and modifications can be made therein without departing from the spirit and scope thereof.

I claim:

1. A method for impeding loss of memory or improving impairment of memory comprising orally administering Mg alone or in combination with another anti-memory loss agent to a subject whose dietary intake of Mg is below the normal intake of about 200 to 450 mg/day, such that the supplemental daily intake of Mg in the subject is in an amount of from about 200 to 1,620 mg/day.

2. The method as claimed in claim 1, wherein said supplemental daily intake of Mg in the subject is from about 300 to 1,260 mg/day.

3. The method as claimed in claim 1, wherein said Mg is orally administered in the form of a food containing high concentrations of Mg selected from the group consisting of regular or skim milk, bran flakes, cream of wheat, oatmeal, puffed wheat, shredded wheat, whole wheat bread, shrimp, grape juice, grapefruit juice, orange juice, pineapple juice, prune juice, tomato juice, asparagus, beets, broccoli, carrots, corn, peas, tomatoes, potatoes, bananas, cherries, oranges, pineapples, and mixtures thereof.

4. The method as claimed in claim 9, wherein said Mg is orally administered in the form of a pharmaceutically acceptable Mg compound selected from the group consisting of Mg sulfate, Mg oxide, Mg chloride, Mg lactate, Mg citrate, Mg hydroxide, and mixtures thereof.

5. The method as claimed in claim 1, wherein said another anti-memory loss agent is selected from the group consisting of NaF, THA, physostigmine, choline chloride, lecithin, and mixtures thereof.

6. The method as claimed in claim 5, wherein said NaF is orally administered in an amount of from about 0.5 to 1.0 mg/kg of body weight/day.

7. The method as claimed in claim 5, wherein said NaF is orally administered in an amount of from about 40 to 60 mg/day.

8. The method as claimed in claim 5, wherein said THA is orally administered in an amount of from about 25 to 200 mg/day.

9. The method as claimed in claim 8, wherein said THA is orally administered in an amount of from about 150 to 200 mg/day.

10. The method as claimed in claim 5, wherein said physostigmine is orally administered in an amount of from about 2 to 16 mg/day, divided into 6 to 8 doses/day.

11. The method as claimed in claim 10, wherein said physostigmine is orally administered in an amount of from about 4 to 16 mg/day, divided into 6 to 8 doses/day.

12. The method as claimed in claim 5, wherein said chlorine chloride is orally administered in an amount of from about 1,200 to 14,400 mg/day.

13. The method as claimed in claim 12, wherein said choline chloride is orally administered in an amount of from about 9.600 to 12.000 mg/day.

14. The method as claimed in claim 5, wherein lecithin is orally administered in an amount of from about 1,200 to 14,400 mg/day.

15. The method as claimed in claim 14, wherein said lecithin is orally administered in an amount of from about 9,600 to 12,000 mg/day.

16. A method for impeding loss of memory or improving impairment of memory comprising orally administering Mg alone or in combination with another anti-memory loss agent to a subject whose dietary intake of Mg is the normal intake of about 200 to 450 mg/day, such that the supplemental daily intake of Mg in the subject is in an amount of from about 540 to 1,620 mg/day.

17. The method as claimed in claim 16, wherein said supplemental daily intake of Mg in the subject is from about 840 to 1,260 mg/day.

18. The method as claimed in claim 16, wherein said Mg is orally administered in the form of a food containing high concentrations of Mg selected from the group consisting of regular or skim milk, bran flakes, cream of wheat, oatmeal, puffed wheat, shredded wheat, whole wheat bread, shrimp, grape juice, grapefruit juice, orange juice pineapple juice, prune juice, tomato juice, asparagus, beets, broccoli, carrots, corn, peas, tomatoes, potatoes, bananas, cherries, oranges, pineapples, and mixtures thereof.

19. The method as claimed in claim 16, wherein said Mg is orally administered in the form of a pharmaceutically acceptable Mg compound selected from the group consisting of Mg sulfate, Mg oxide, Mg chloride, Mg lactate, Mg citrate, Mg hydroxide, and mixtures thereof.

20. The method as claimed in claim 16, wherein said another anti-memory loss agent is selected from the group consisting of NaF, THA, physostigmine, choline chloride, lecithin, and mixtures thereof.

21. The method as claimed in claim 20, wherein said NaF is orally administered in an amount of from about 0.5 to 1.0 mg/kg of body weight/day.

22. The method as claimed in claim 20, wherein said NaF is orally administered in an amount of from about 40 to 60 mg/day.

23. The method as claimed in claim 20, wherein said THA is orally administered in an amount of from about 25 to 200 mg/day.

24. The method as claimed in claim 23, wherein said THA is orally administered in an amount of from about 150 to 200 mg/day.

25. The method as claimed in claim 20, wherein said physostigmine is orally administered in an amount of from about 2 to 16 mg/day, divided into 6 to 8 doses/day.

26. The method as claimed in claim 25, wherein said physostigmine is orally administered in an amount of from about 4 to 16 mg/day, divided into 6 to 8 doses/day.

27. The method as claimed in claim 20, wherein said choline chloride is orally administered in an amount of from about 1,200 to 14,400 mg/day.

28. The method as claimed in claim 27, wherein said choline chloride is orally administered in an amount of from about 9,600 to 12,000 mg/day.

29. The method as claimed in claim 20, wherein said lecithin is orally administered in an amount of from about 1,200 to 14,400 mg/day.

30. The method as claimed in claim 29, wherein said lecithin is orally administered in an amount of from about 9,600 to 12,000 mg/day.

* * * * *

UNITED STATES PATENT AND TRADEMARK OFFICE
CERTIFICATE OF CORRECTION

PATENT NO.   :  5,004,615
DATED        :  April 2, 1991
INVENTOR(S)  :  J. LESLIE GLICK It is certified that error appears in the above-identified patent and that said Letters Patent is hereby corrected as shown below:

Col. 6,  line 33, please delete "A' and A'''" and insert --A' and A"--;

Col. 7,  line 4, Equation (3), please delete "A'''" and insert --A"--;

line 22, please delete "A'A'''" and insert --Q'A"--;

Col. 8,  line 19, please delete "(a)" and insert --($\underline{a}$)--;

line 21, please delete "(m)" and insert --($\underline{m}$)--;

line 31, please delete "m" and insert --m'--;

line 55, please delete "A=A"(A'/A")+A"(12)" and insert --A=A"(A'/A") + A"    (12)--;

line 57, Equation (13), please delete "A"=A/(A"/AΔ+1)" and insert --A"=A/(A'/A"+1)--.

Col. 9,  line 28, please delete "obtain(R)d" and insert --obtained--;

line 34, Equation (14), please delete "aQA" and insert --$\underline{a}$QA--;

line 36, Equation (15), please delete "mQA" and insert --$\underline{m}$QA--;

line 38, please delete "a" and insert --$\underline{a}$--;

line 39, delete m and insert --$\underline{m}$--;

line 40, please delete m/a and insert --$\underline{m}$/$\underline{a}$--;

line 43, Equation (16), please delete "m/s" and insert --$\underline{m}$/$\underline{a}$--;

line 49, Equation (17), please delete "am/ma" and insert --a$\underline{m}$/m$\underline{a}$--;

UNITED STATES PATENT AND TRADEMARK OFFICE
CERTIFICATE OF CORRECTION

PATENT NO. : 5,004,615

DATED : April 2, 1991

INVENTOR(S) : J. LESLIE GLICK

It is certified that error appears in the above-identified patent and that said Letters Patent is hereby corrected as shown below:

Col. 11, line 36, delete "Trapp" and insert --Trapp,--;

Col. 12, line 54, Claim 4, delete "claim 9" and insert --claim 1--;

Col. 13, line 44, claim 18, please delete "juice pineapple" and insert --juice, pineapple--.

Signed and Sealed this

Eighth Day of September, 1992

Attest:

DOUGLAS B. COMER

*Attesting Officer*     Acting Commissioner of Patents and Trademarks